United States Patent [19]

Lees

[11] Patent Number: 4,660,563
[45] Date of Patent: Apr. 28, 1987

[54] METHOD AND MEANS FOR DETECTION OF ARTERIAL LESIONS

[75] Inventor: Robert S. Lees, Brookline, Mass.

[73] Assignee: Massachusetts Institute of Technology, Cambridge, Mass.

[21] Appl. No.: 775,093

[22] Filed: Sep. 11, 1985

Related U.S. Application Data

[63] Continuation of Ser. No. 686,633, Dec. 31, 1984, abandoned, which is a continuation of Ser. No. 425,187, Sep. 28, 1982, abandoned.

[51] Int. Cl.$^4$ .............................................. A61B 6/00
[52] U.S. Cl. ................................................... 128/654
[58] Field of Search ......................................... 424/1.1

[56] References Cited

U.S. PATENT DOCUMENTS 4,343,734 8/1982 Lian et al. ............................. 424/1.1
4,359,453 11/1982 Gordon ................................. 424/1.1

OTHER PUBLICATIONS

Höhne, K. H., *Digital Image Processing Proceedings*, Hamburg, 10-5-1981, Springer-Verlag, Berlin, Hamburg, N.Y., 1981.
Roberts, A. B. et al, "LDLs Concentrate in Damaged Arterial Wall", 53rd Scientific Sessions, Nov. 17–20, 1980, Miami Beach, Fla.
Wilhelmsen, Lars, "Fibrinogen as Risk Factor for Stroke and MI", NEJM, vol. 311, No. 8, Aug. 23, 1984.
Yano, Y. et al, "Myocardial Uptake Studies with 124 Cs and the Scintillation Camera", J. Nucl. Med. (USA) vol. 11, No. 11, Nov. 1970.

*Primary Examiner*—Kyle L. Howell
*Assistant Examiner*—Francis J. Jaworski
*Attorney, Agent, or Firm*—Cesari and McKenna

[57] ABSTRACT

The atherosclerotic plaques which form arterial lesions have been found to take up lipoproteins from the blood flowing through the arteries. Accordingly, the early detection of arterial disease is accomplished by preparing an infusate composed of radiolabeled low-density lipoproteins and introducing the infusate into the patient's arterial system. A gamma radiation detector is then used to detect and quantify concentrations of the radiolabeled proteins thereby to indicate the locations and sizes of the lesions.

8 Claims, 1 Drawing Figure

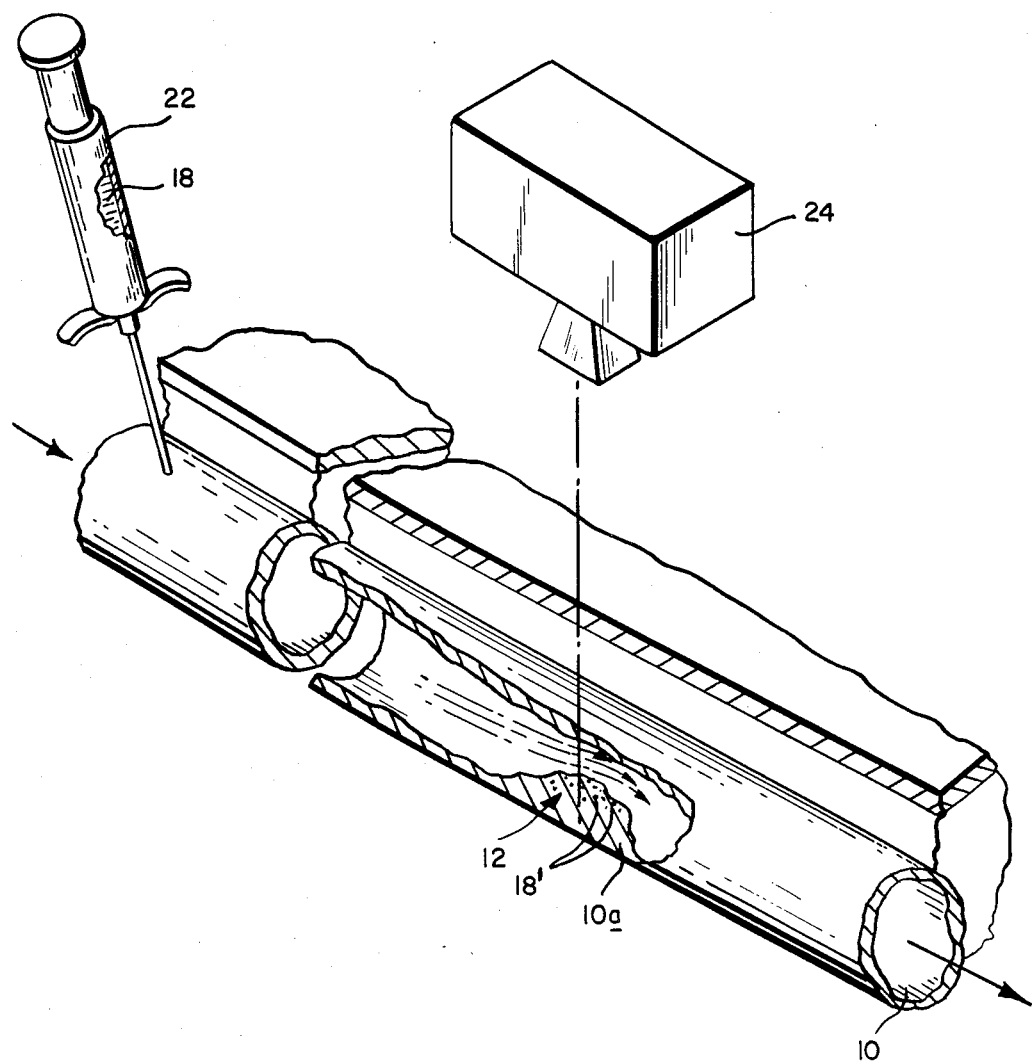

METHOD AND MEANS FOR DETECTION OF ARTERIAL LESIONS

This application is a continuation of application Ser. No. 686,633, filed Dec. 31, 1984 now abandoned which application is a continuation of application Ser. No. 425,187, filed Sept. 28, 1982, now abandoned.

This invention relates to method and means for the detection of arterial lesions and particularly human atherosclerotic lesions.

BACKGROUND OF THE INVENTION

Arterial disease, primarily atherosclerosis is a major cause of death in many industrially advanced countries. This condition is caused by the build-up in a blood vessel of atherosclerotic plaques. The resultant stenosis occludes the vessel, thereby reducing the flow of blood to the brain and other vital organs, as well as placing undue strain on the wall of the vessel. Arterial sclerosis is inevitable with aging and is usually clinically silent until relatively far advanced, a characteristic which tends to frustrate attempts at early clinical diagnosis. Since means do exist for delaying and reducing the incidence of vascular occlusion, the early detection of arterial atheromatous plaque in critical vessels is of considerable value in that it would permit the application of such preventive interventions at a time when they could be most effective.

In the past, study of the atherosclerotic process in man has been difficult. The state of the arteries for diagnostic and investigative purposes has been assessed directly by vascular catheterization and arteriography. However, that technique is uncomfortable for the patient and it is invasive in that it entails risk of infection, bleeding and arrhythmia. There do exist various more or less noninvasive techniques for the diagnosis of arterial disease. These techniques include plethysmography, thermoraphy and ultrasound scanning, all of which are described briefly in the article *Noninvasive Diagnosis of Arterial Disease*, by Robert S. Lees and Gordon S. Myers, Annals of Internal Medicine, Vol. 27 (1982), pp. 475–509. While the aforesaid diagnostic tools do assist in the diagnosis of arterial disease, they are not able to recognize and quantify preclinical arterial disease reliably enough to determine the need for surgery or medical therapy. In other words, they do not detect the disease early enough to enable the physician to treat the disease by nonsurgical means such as by prescribing drugs or a proper diet. As a result, those prior procedures are used primarily to assist the physician to make a clinical decision as to whether or not a particular patient should undergo arteriography to define the need for surgery. Also, those prior more or less noninvasive diagnostic techniques are not accurate and reliable enough to be used to evaluate the efficiency of the various known long-term nonsurgical treatments for such vascular disease.

SUMMARY OF THE INVENTION

Accordingly, the present invention aims to provide a method for early detection of vascular disease.

Another object of the invention is to provide such a method which does not involve surgical invasion of the patient's body.

A further object of the invention is to provide an improved method of locating and quantifying arterial lesions.

A further object is to provide a method of evaluating noninvasively the efficacy of various treatments for vascular disease such as atherosclerosis.

Still another object of the invention is to provide apparatus for assisting in the early detection of and quantifying of vascular disease.

Other objects will, in part, be obvious and will, in part, appear hereinafter.

The invention accordingly comprises the several steps and the relation of one or more of steps with respect to each of the others, and the apparatus embodying the features of construction, combination of elements and arrangement of parts which are adapted to effect such steps, all as exemplified in the following detailed description, and the scope of the invention will be indicated in the claims.

Briefly, my invention resides in the discovery for the first time that atherosclerotic plaques which accumulate in the subintimal layers of arteries, particularly the carotid artery, to form arterial lesions, tend to take up lipoproteins from the blood circulating in the arteries. Thus by measuring the lipoprotein concentration along an artery, an area of disease in that artery can be located and should be able to be quantified.

To accomplish this, the patient is injected with low-density lipoproteins which are radiolabeled with an appropriate radionuclide such as In-111 or Tc-99m; also, I-125 has been used in pilot studies. Then the patient is viewed with a standard gamma camera or other type of gamma radiation detector which detects the radioactive concentration at, and thus locates the site of, each arteriosclerotic lesion and measures the rate of uptake and degree of concentration of the radiolabeled protein in each lesion. That, in turn, provides an accurate indication of the actual location of each area of disease, its extent and therefore its potential effect on arterial blood flow.

Thus, my discovery and method of applying it diagnostically facilitate the early detection of arterial lesions extracorporeally and without invading the patient's body other than for the injection of the labeled lipoprotein. My procedure can be accomplished quickly without causing patient trauma and, accordingly, it should prove to be a valuable diagnostic tool for early preclinical detection of vascular disease such as atherosclerosis. The same technique can also be employed to evaluate various long-term treatments for vascular disease.

BRIEF DESCRIPTION OF THE DRAWING

For a fuller understanding of the nature and objects of the invention, reference should be had to the following detailed description, taken in connection with the accompanying drawing FIGURE is a diagrammatic view of a patient's artery cut-away to show a stenotic lesion and apparatus for practicing the method of this invention.

DESCRIPTION OF THE PREFERRED EMBODIMENT

Referring to the drawing FIGURE, there is shown there the artery 10 of a patient. The artery is diseased in that a stenotic lesion 12 is forming in the subintimal layer of the arterial wall 10a. The lesion 12 thus partially occludes the artery, thereby slowing the flow of blood and increasing the pressure on the arterial wall upstream from the lesion. If left undetected, the stenosis 12 could in time completely occlude the artery, stopping the flow of blood entirely.

In accordance with my procedure, radiolabeled lipoproteins 18, preferably low-density lipoproteins, are infused into the patient's arterial system using a standard hypodermic syringe 22.

The infused lipoproteins are obtained from human blood which may or may not be from the patient being tested. The lipoproteins in the blood are separated by differential ultracentrifugation into different density classes. A low-density class of densities of 1.025 to 1.050 gm/ml is selected and labeled with a suitable radioisotope, which may be, for example, Tc-99m, In-111, I-125 or I-123. Then the patient is viewed with an appropriate gamma radiation detector such as a gamma or Anger camera 24 positioned over the patient.

I have found that the lipoproteins 18 circulating through the artery 10 tend to concentrate in the atherosclerotic plaques that accumulate to form the lesion 12. A short period of time after infusion of the radiolabeled lipoproteins 18, there begins to be an appreciable uptake of the tagged proteins at the lesion 12 as indicated at 18' in the drawing FIGURE. The radiation emitted by those radiolabeled proteins 18' is imaged by camera 24 so that the site of the lesion 12 is readily ascertainable. The radio-tracer 18 deposition is then quantified in the usual way with a computer. In addition, by viewing the lesion 12 at spaced time intervals with camera 24, the rate of uptake of the radiolabeled proteins 18' at any given time can be ascertained.

Correlation between the radio tracer deposition and the actual size of the lesion for developing a data base can be obtained by comparing these results with those obtained by arteriography, or by autoradiography on vessel segments removed from patients during surgery.

In a working example of our diagnostic procedure, the two carotid arteries of each of four subjects were studied, three with carotid atherosclerosis and one with normal carotid arteries. The subjects were each injected with 100 microcuries I-125-low-density lipoproteins (I-125-LDL). Then, anterior or lateral views of the neck of each subject were made at six hour, one day and two day intervals using a Technicare Series 420 Scintillation camera and Series 550 computer. These views were compared with the three patients' carotid arteriograms and duplex doppler ultrasound scans in the case of the control subject. Of the six diseased carotid bifurcations studied at two days, unequivocal focal I-125-LDL accumulation was seen in four vessels and very probable accumulation in two vessels. In each case, the localization corresponded exactly to the disease as seen on arteriography. The disease at three of the six arterial bifurcations was asymptomatic.

Also, the ratio of focal accumulation to background blood-pool radioactivity in each subject increased steadily from six hours to two days, becoming as high as 3:1, even though maximum lesion uptake was less than 0.1 percent of the administered dose to each subject.

Uninvolved areas in the same vessels and in both carotids of the control subject showed no detectable radioactivity beyond a faint blood-pool image.

Using my diagnostic technique, then, extracorporeal imaging of even asymptomatic human atherosclerosis is made possible and may allow early diagnosis of occult arterial disease. Accordingly, the technique should permit early intervention to delay or reduce the incidence of vascular occlusion. It should also facilitate the evaluation of long-term treatments for such vascular disease.

It will thus be seen that the objects set forth above, among those made apparent from the preceding description, are efficiently attained. Also, certain changes may be made in carrying out the above method and in the above construction without departing from the scope of the invention. For example, instead of using a conventional gamma camera, it is also possible to detect with greater sensitivity and follow more accurately the radiolabeled lipoprotein uptake at lesion 12 by the use of scintillation cross-sectional or tomography techniques to view the lesion. Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. The method for the early detection of arterial disease including atherosclerosis comprising the steps of
   A. preparing an infusate composed of
      1. low density lipoproteins, and
      2. tracer means linked to said proteins and capable of being viewed extracorporeally,
   B. injecting the infusate into the vascular system of a patient;
   C. subsequently viewing the patient's vascular system with extracorporeally-located detecting means capable of detecting the tracer means;
   D. determining from said detecting means the locations of tracer means in the patient's vascular system; and
   E. quantifying concentrations of the tracer means by said detecting means at one or more of said locations.

2. The method defined in claim 1 wherein the infusate is prepared from lipoproteins having a density of from 1.025 to 1.050 gm/ml.

3. The method defined in claim 1 wherein
   A. The infusate is preapred from tracer means composed of a radionuclide; and
   B. the determining step is accomplished by viewing the vascular system with a gamma radiation detector.

4. The method defined in claim 3 wherein the infusate is prepared from a radionuclide selected from the class consisting of Tc-99m, In-111, I-125 and I-123.

5. Apparatus for detecting vascular disease comprising
   A. an infusate for infusing into the vascular system of a patient, said infusate including
      1. low density blood lipoproteins having a selected density range; and
      2. tracer means linked to said proteins and capable of being viewed estracorporeally;
   B. tracer detecting means for positioning opposite the patient's body to detect concentrations of said tracer means in said vascular system; and
   C. means for quantifying the detected tracer means concentrations.

6. The apparatus defined in claim 5 wherein the lipoproteins have a density of 1.025 to 1.050 gm/ml.

7. The apparatus defined in claim 5 wherein
   A. the tracer means is a radionuclide; and
   B. the detecting means responds to gamma radiation.

8. The apparatus defined in claim 7 wherein the radionuclide is selected from the group consisting of Tc-99m, In-111, I-125 or I-123.

* * * * *